United States Patent
Anderson et al.

(10) Patent No.: US 8,298,258 B2
(45) Date of Patent: Oct. 30, 2012

(54) EMBOLIC PROTECTION DEVICE

(75) Inventors: James Anderson, Fridley, MN (US);
Erin Guest, Minneapolis, MN (US);
Benjamin Arcand, Minneapolis, MN (US)

(73) Assignee: Boston Scientific Scimed, Inc, Maple Grove, MN (US)

( * ) Notice: Subject to any disclaimer, the term of this patent is extended or adjusted under 35 U.S.C. 154(b) by 42 days.

(21) Appl. No.: 12/573,553

(22) Filed: Oct. 5, 2009

(65) Prior Publication Data

US 2011/0082492 A1    Apr. 7, 2011

(51) Int. Cl.
*A61M 29/00* (2006.01)

(52) U.S. Cl. ........................................................ 606/200

(58) Field of Classification Search .................. 606/200, 606/108, 113, 114, 159, 198; 604/104–107
See application file for complete search history.

(56) References Cited

U.S. PATENT DOCUMENTS

| | | | |
|---|---|---|---|
| 5,108,419 A * | 4/1992 | Reger et al. | 606/200 |
| 6,129,739 A * | 10/2000 | Khosravi | 606/200 |
| 6,540,768 B1 | 4/2003 | Diaz et al. | |
| 6,544,279 B1 | 4/2003 | Hopkins et al. | |
| 6,610,077 B1 | 8/2003 | Hancock et al. | |
| 6,726,701 B2 | 4/2004 | Gilson et al. | |
| 7,014,647 B2 | 3/2006 | Brady et al. | |
| 7,144,408 B2 | 12/2006 | Keegan et al. | |
| 7,229,462 B2 | 6/2007 | Sutton et al. | |
| 7,229,463 B2 | 6/2007 | Sutton et al. | |
| 7,410,491 B2 | 8/2008 | Hopkins et al. | |
| 7,537,600 B2 | 5/2009 | Eskuri | |
| 2003/0195555 A1 | 10/2003 | Khairkhahan et al. | |
| 2007/0060947 A1* | 3/2007 | Beulke et al. | 606/200 |
| 2008/0243170 A1 | 10/2008 | Jenson et al. | |
| 2008/0255606 A1 | 10/2008 | Mitra et al. | |

* cited by examiner

*Primary Examiner* — Elizabeth Houston
(74) *Attorney, Agent, or Firm* — Seager, Tufte & Wickhem LLC

(57) ABSTRACT

The invention provides an embolic filter, a support structure therefor, and methods for preparing said filter for deployment and retrieval.

10 Claims, 7 Drawing Sheets

EMBOLIC PROTECTION DEVICE

TECHNICAL FIELD

This disclosure relates generally to embolic filters, support structures therefor, and methods for preparing said filters for deployment and retrieval.

BACKGROUND

Human blood vessels often become occluded or blocked by plaque, thrombi, other deposits, or material that reduce the blood carrying capacity of the vessel. Should the blockage occur at a critical place in the circulatory system, serious and permanent injury, and even death, can occur. To prevent this, some form of medical intervention is usually performed when significant occlusion is detected.

Several procedures are now used to open these stenosed or occluded blood vessels in a patient caused by the deposit of plaque or other material on the walls of the blood vessels. Angioplasty, for example, is a widely known procedure wherein an inflatable balloon is introduced into the occluded region. The balloon is inflated, dilating the occlusion, and thereby increasing the intraluminal diameter.

Another procedure is atherectomy. During atherectomy, a catheter is inserted into a narrowed artery to remove the matter occluding or narrowing the artery, i.e., fatty material. The catheter includes a rotating blade or cutter disposed in the tip thereof. Also located at the tip are an aperture and a balloon disposed on the opposite side of the catheter tip from the aperture. As the tip is placed in close proximity to the fatty material, the balloon is inflated to force the aperture into contact with the fatty material. When the blade is rotated, portions of the fatty material are shaved off and retained within the interior lumen of the catheter. This process is repeated until a sufficient amount of fatty material is removed and substantially normal blood flow is resumed.

In another procedure, stenosis within arteries and other blood vessels is treated by permanently or temporarily introducing a stent into the stenosed region to open the lumen of the vessel. The stent typically includes a substantially cylindrical tube or mesh sleeve made from such materials as stainless steel or nitinol. The design of the material permits the diameter of the stent to be radially expanded, while still providing sufficient rigidity such that the stent maintains its shape once it has been enlarged to a desired size.

Such percutaneous interventional procedures, i.e., angioplasty, atherectomy, and stenting, can dislodge material from the vessel walls. This dislodged material can enter the bloodstream. Some existing devices and technology use a filter for capturing the dislodged material from the bloodstream.

SUMMARY

This disclosure pertains to an embolic filter adapted to conform to a range of vessel diameters in a deployed state as well as to function in vessels which depart from an idealized circular cross-section.

In a first embodiment, the filter comprises a first hub having an axial lumen therethrough, said lumen defining a longitudinal axis of the filter and adapted to receive a guidewire therethrough and a second hub having an axial lumen therethrough, said lumen coinciding with the longitudinal axis of the filter and adapted to receive a guidewire therethrough wherein the first and second hubs are displaced from each other along the longitudinal axis. The filter includes a first plurality of struts each having a first end, a second end, and a length with the first ends of each strut being directly connected to the first hub. The second ends of the first plurality of struts are biased to expand away from the longitudinal axis of the filter. A second plurality of struts each having a first end, a second end, and a length is directly connected to the second hub at their first end. The second ends of the second plurality of struts are also biased to expand away from the longitudinal axis of the filter. The lengths of the first plurality of struts are substantially the same as the lengths of the second plurality of struts and the two pluralities of struts assume equivalent angles with the longitudinal axis in an expanded state. In addition, at least a first population and a second population of arcuate support elements are directly connected to the second ends of the respective first and second pluralities of struts such that each population of support elements defines a plane generally transverse to the longitudinal axis of the filter, said planes being relatively displaced along the longitudinal axis of the filter. The filter includes a filter sac attached at its open end to the support elements, the sac extending beyond the planes of the support elements in at least one of a proximal or distal direction. The filter includes at least one band element slidable over the hubs and a portion of the struts thereby moving those portions of the struts which are coupled to the support elements closer to the longitudinal axis of the filter and a control element attached to the band, said control element adapted to move the band along the longitudinal axis of the filter and over at least a portion of the longitudinal struts.

In one variation, the filter comprises a single hub having an axial lumen therethrough, said lumen defining a longitudinal axis of the filter and adapted to receive a guidewire. At least two pluralities of generally longitudinal struts each having a first end and a second end are directly connected to the hub at their first ends and the said second ends of the struts being biased to expand away from the longitudinal axis of the filter. A first and second group of arcuate support elements are directly connected to the second ends of the respective at least two pluralities of generally longitudinal struts such that each group of arcuate support elements defines a plane transverse to the longitudinal axis of the filter, said planes being relatively displaced along the longitudinal axis of the filter. The filter includes at least one band element slidable over the hub and a portion of the struts thereby moving those portions of the struts which are coupled to the support elements closer to the longitudinal axis of the filter and a control element attached to the band, said control element adapted to move the band along the longitudinal axis of the filter and over at least a portion of the longitudinal struts.

In each of the embodiments, the embolic filter includes sets of generally coplanar and spaced-apart support elements which are individually capable of expanding from a first delivery configuration adjacent to a guidewire to a deployed configuration in which they contact the vessel wall and which, in combination with spanning edges of a filter sac, form a mouth of the filter. The support elements are directly coupled to and support segments of the filter sac. The individual support elements within a group allow the filter to adjust to a variety of vessel diameters and cross-sectional shapes while free edges of the filter sac flexibly bridge nearly axial gaps between the spaced-apart support elements. The geometry of the grouped struts and associated support elements allow the mouth of the filter sac to rearrange its supported and unsupported segments to closely approximate the circumference of a variety of vessels.

DETAILED DESCRIPTION

The following description should be read with reference to the drawings wherein like reference numerals indicate like elements throughout the several views. The drawings, which are not necessarily to scale, are not intended to limit the scope of the claimed invention. The detailed description and drawings illustrate example embodiments of the claimed invention.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

The embolic filters 10 disclosed herein can include a guidewire 80, or tube, and may be advanced through a blood vessel 20 until they are positioned downstream of an obstruction to be treated. The filters are then deployed by withdrawing a strut confining band 92. (Band 92 and associated control element 94 have been omitted from some of the figures for clarity.) The filters include several struts, 42 and 44, which tend to bias a filter sac 70 consisting of a porous sheet or mesh in the form of a cone or basket toward an expanded position which completely spans the lumen of the vessel to be protected. Some struts 44 may be obscured by the guidewire 80 in certain of the drawings. Supported and unsupported regions of the filter sac's upstream edge alternate circumferentially with the supported regions lying generally in two or more spaced-apart and parallel planes while the unsupported regions of the edge are generally axially disposed and helically wrap along the vessel wall. When the procedure has been completed, the filter is withdrawn by at least partially collapsing the filter, by advancing control element 94 and band 92 over the struts, to contain any captured emboli or other debris while the filter is withdrawn from the vessel. Although the filters are well suited to be employed without a delivery or retrieval sheath, it will be appreciated that they may be used with a sheath if desired. In some embodiments, the band and control element may be replaced by a sheath.

Figure 1A:
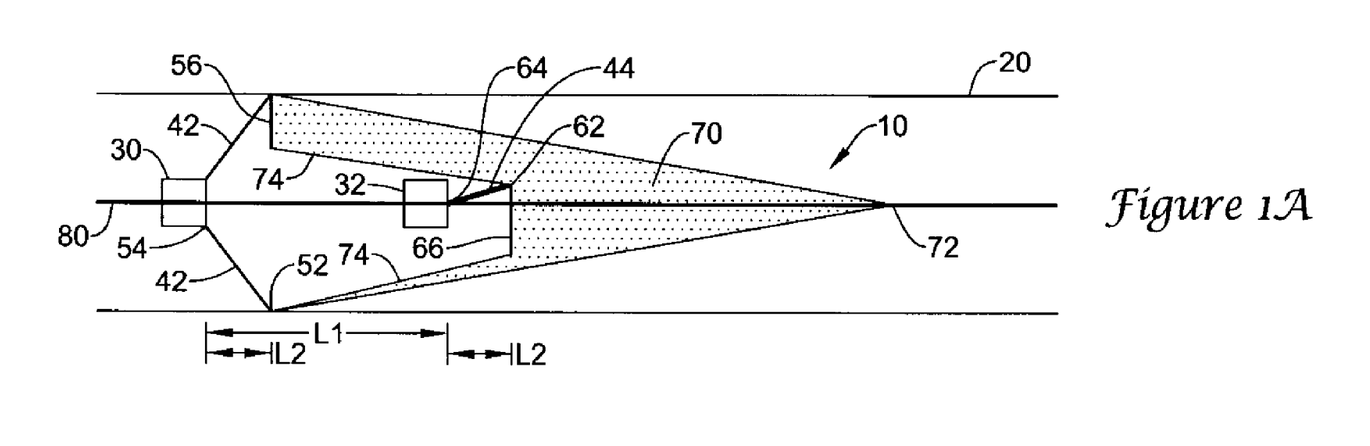
FIG. 1A is a somewhat schematic longitudinal cross-sectional view of an embodiment of the invention deployed in a vessel.
Figure 1B:
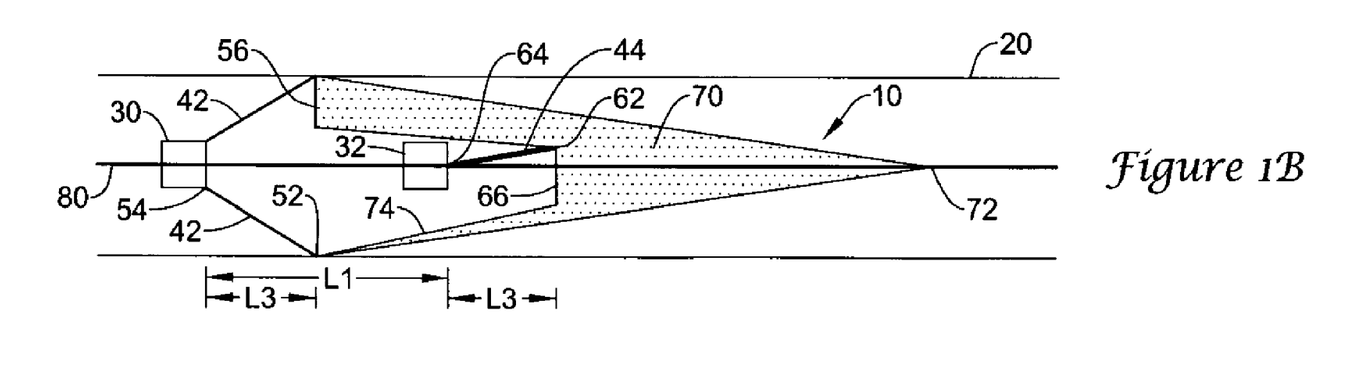
FIG. 1B is a somewhat schematic longitudinal cross-sectional view of the embodiment of FIG. 1 deployed in a different vessel.
Figure 4:
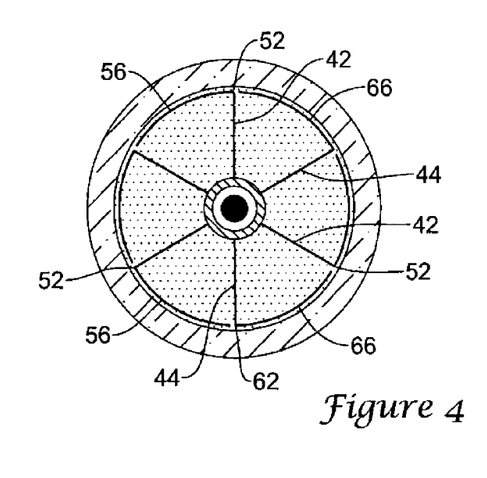
FIG. 4 is a somewhat schematic axial view in the distal direction of an embodiment of the invention deployed in a vessel.

The filter 10 of FIGS. 1A and 1B is shown in deployed states in vessels of two different nominal diameters. Hubs 30 and 32 are fixed to guidewire 80. For the purpose of illustration, each hub has two struts attached thereto. In other embodiments, a greater number of struts and/or a greater number of hubs may be employed. When more struts and/or more hubs are employed the struts of one hub will generally be sequentially interleaved in an offset circumferential distribution with the struts of successive hubs, as shown in FIGS. 2 and 4. The struts of FIGS. 1A-D are directly attached at their first end to their respective hubs. Thus two struts 42 are attached to hub 30 at first ends 54 and two struts 44 are attached to hub 32 at first ends 64. The distal ends of struts 42 are attached to support segments 56 at an end 52 thereof and the distal ends of struts 44 are attached to support segments 66 at an end 62 in a similar manner. Due to the cross-sectional view presented, struts 44 of each drawing would lie partially behind guidewire 80 and/or tubular element 34 and so would not be fully visible. For purposed of illustration, the width of strut 44 in each of FIGS. 1A-1D has been exaggerated to make it more readily visible. Further, FIG. 1D includes a proximal band 92 and control element 94, omitted from FIGS. 1A-C for clarity and a band 92 and control element 94, to be discussed later, associated with distal hub 34.

Figure 12:
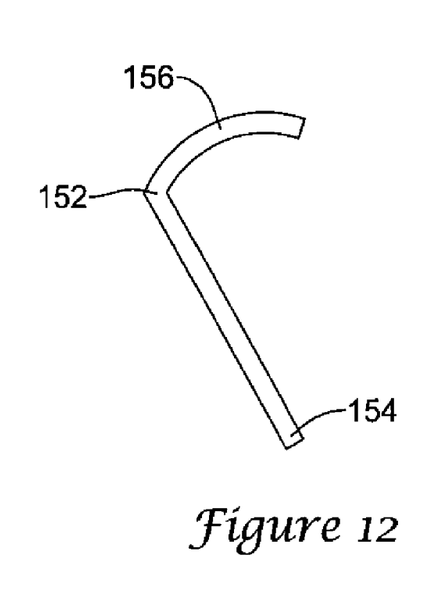
FIG. 12 is an illustrative example of a strut of the invention.

The second ends of the struts are attached to support elements which may assume a variety of configurations. As illustrated in FIGS. 1A-B, each strut and its associated support element may take a generally "L"-shape in which the short leg of the "L" is disposed at a right angle to the strut and assumes a curved shape, as shown in FIG. 12, which allows it to lie along the vessel wall in a deployed configuration. In these embodiments, the filter sac is attached to the shorter curved leg of the "L" and includes unsupported, generally axial free edges 74 which bridge the gaps between successive support elements. FIG. 4 illustrates an embodiment in which two hubs each have three "L"-shaped struts and support elements which alternate circumferentially around the mouth of the filter sac 70 with nearly axial free edges 74 of the sac.

Figure 13:
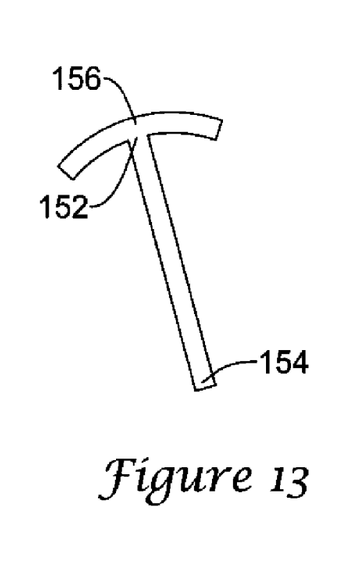
FIG. 13 is an illustrative example of a strut of the invention.
Figure 14:
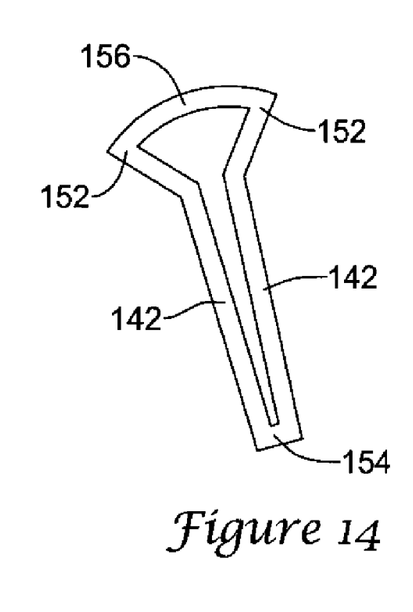
FIG. 14 is an illustrative example of a strut of the invention.

In other embodiments, a strut and its associated support element may take a generally "T"-shape in which the top of the "T" is disposed at a right angle to the longer strut and assumes a curved shape which allows it to lie along the vessel wall in a deployed configuration. See FIG. 13. In yet other embodiments, a support element may bridge two struts as illustrated in FIG. 14. In bridged strut configurations, the struts of a pair should be relatively close to parallel to each other in order to reduce the inside diameter of the capture element which will surround at least a portion of the struts in the delivery and retrieval configurations. Optionally, the struts of a pair may be adapted to flex or pivot toward each other near the hub to further reduce the inside diameter of the capture element and/or the force required to advance and withdraw the capture element. Other configurations of the support elements are also contemplated. In addition, combinations of support element configurations may be employed.

Depending upon the diameter of the vessel in which the filter will be deployed, it may be desirable to select support members which are curved to approximate the curvature of the wall 20 of the vessel or to form the support members from a material which has sufficient flexibility to conform to the vessel walls having different diameters. In some embodiments, a support element and strut may be formed as an integral unit as by appropriately bending a wire or by molding the combination. In other embodiments, the support element may be attached to its strut or struts by welding, adhesives, and the like. It is desirable that at least the strut portion of a strut/support element unit be biased to assume a position in which the second end of the strut is positioned away from the longitudinal axis of the filter when it is not constrained. Suitable materials for the struts and/or support elements include biologically compatible metals and polymers. The materials may be elastically resilient or may include shape memory materials such as nitinol. In certain embodiments, the struts may be caused to assume a deployed configuration in which the second ends of the struts are positioned away from the longitudinal axis by other means known in the art, for example by wedges associated with the band which force the struts radially outward as the band is withdrawn by the control element.

As mentioned above, each of the struts of a multi-hub embodiment are nominally of the same length although slight length variations may be introduced within a group of struts attached to a common hub to facilitate improved packing of the attached support elements in the delivery and retrieval configurations. When the expanded filter configuration includes small circumferential gaps or overlaps between support elements, as viewed along the longitudinal axis of the filter, the combination of the guidewire 80, a strut/support member 42/56 attached to a first hub 30, a generally longitudinal unsupported edge of the filter material 74, and a strut/support member 44/66 attached to a second hub 32 form a good approximation of a four-bar linkage and the slight lateral shift of the first strut/support member relative to the second strut/support member as the filter adapts to the vessel within which it is deployed will not significantly change the length of unsupported filter material edge disposed between the first and second support members. Comparing FIGS. 1A and 1B, it may be seen that the distance, L1, between corresponding points on hubs 30 and 32 remains essentially the same as the distance between the support segments 56 and 66 as the struts expand outwardly to have a projected axial length L2 in FIG. 1A and a projected axial length L3 in FIG. 1B. Because the unsupported edges 74 remain nearly longitudinally oriented along the vessel wall, their lengths differ by a relatively small amount, often less than a few percent, between the two configurations and the small difference may be compensated for by providing a filter sac material having a modest elasticity or by slightly shortening one set of struts so that the angle formed between the first set of struts and the filter axis differs slightly from the angle formed by the second set of struts and the filter axis in vessels of different diameters.

The unsupported edge length change upon filter expansion may be further minimized in both the multi-hub configuration described above and in the single hub variation to be described below by employing support segments which together form a better approximation of a complete circle, as viewed along the longitudinal axis of the filter, which tends to allow the unsupported edge to lie more nearly parallel to the axis of the filter rather than tilting and assuming a helical configuration. In addition, the relative unsupported edge length change may also be minimized somewhat by increasing the separation between the planes formed by the proximal and distal support segment groups. These modifications result in unsupported edge segments which are more nearly parallel to the axis of the filter and thus need only tilt moderately as the support elements spread to contact the vessel wall. Similar principles apply to the single hub embodiments described in greater detail below since the positions of the deployed support members are similar; however in those embodiments the axial offset between the planes of support elements is obtained by using a first plurality of struts 142 having a first length and a second plurality of struts 144 having a second length.

As illustrated, the filter sac 70 comprises a conventional flexible mesh, nonwoven, or perforated membrane having a generally conical or bucket shape. The membrane may have a plurality of openings sized to allow blood cells to pass while retaining emboli and other undesirable debris. The filter sac is attached to the sac support elements 56 at the ends of struts 42 and to the support elements 66 and the ends of the struts 44. Optionally, the closed end of the sac 72 may be fixed to the guidewire or may be free to rotate about the guidewire 80. Between attachments to the support elements, the edges 74 of the sac are free to flex. Together, the support elements 56, 66 and edges 74 of the filter sac 70 form a mouth of the filter in which the support elements define alternately proximal and distal extents of the mouth and the edges 74 join those extents with generally longitudinal segments.

Although the arrangement of the struts suffices to allow the mouth of the filter sac to expand to maintain circumferential contact between the filter mouth and the vessel wall, it may be desirable to select a sac material with a moderate degree of elasticity especially if a larger range of vessel diameters is to be accommodated. A degree of sac elasticity is also more desirable as the circumferential gaps and/or overlaps between the support elements, as viewed along the longitudinal axis of the filter, become greater. For example, in the embodiment of FIG. 2 in which the support elements are separated by a larger gap than in FIG. 4, which has a larger number of smaller gaps, elasticity is more desirable. When the support elements are viewed along the longitudinal axis of the filter, they may appear to form a complete circle in which they overlap or an incomplete circle with small gaps. In some embodiments, the elements may appear to be slightly overlapped when the filter is deployed in a small vessel and may appear to have circumferential gaps when the filter is deployed in a larger vessel. Selecting support element lengths such that the overlaps are similar to the gaps in the support elements for the extremes of vessel diameters in which the filter may be deployed will tend to minimize the difference in the length of unsupported edges 74 to be spanned between proximal and distal support elements. Relatively inelastic sac material may be used if the unsupported edges 74 are longer and more nearly axially aligned.

Figure 1C:
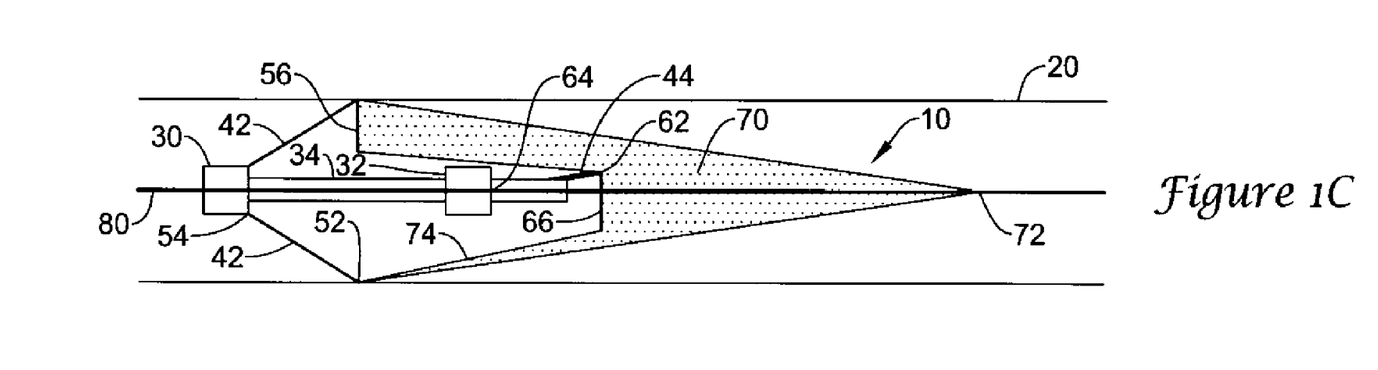
FIG. 1C is a somewhat schematic longitudinal cross-sectional view of related embodiment of the invention deployed in a vessel.
Figure 1D:
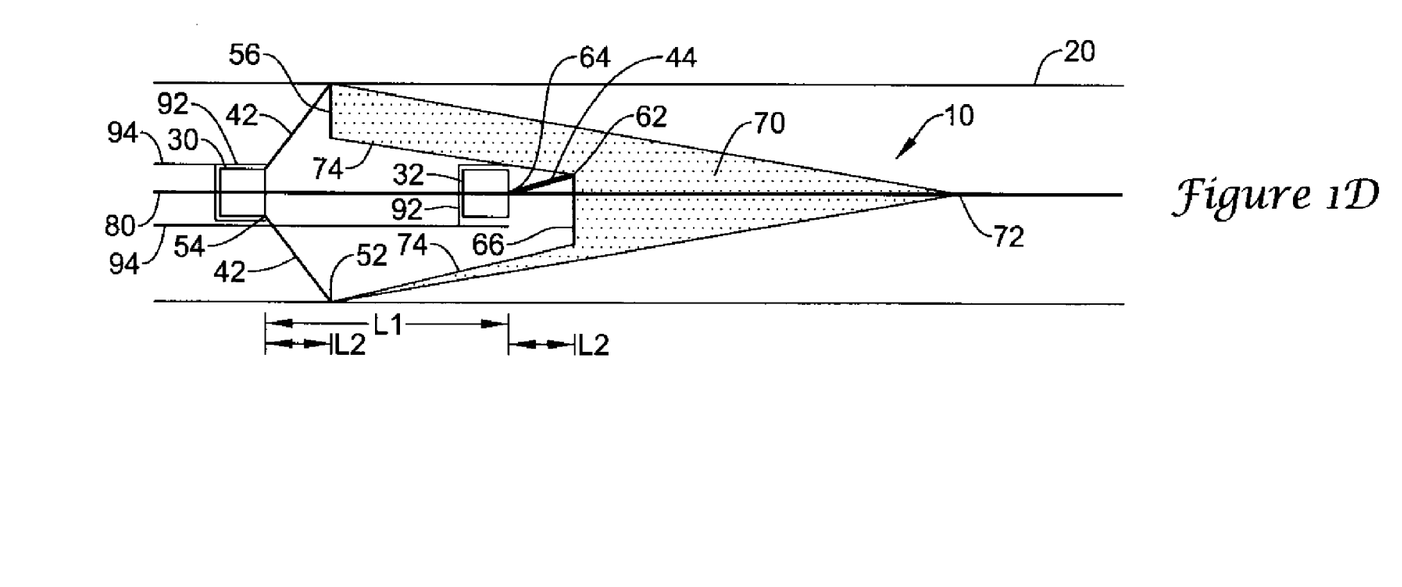
FIG. 1D is a somewhat schematic longitudinal cross-sectional view of the embodiment of FIG. 1A including additional detail.
Figure 2:
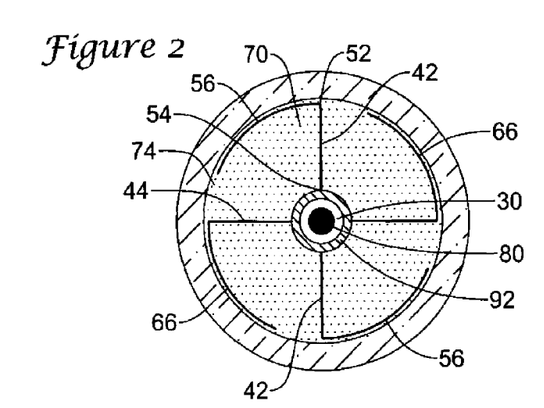
FIG. 2 is a somewhat schematic axial view in the distal direction of an embodiment of the invention deployed in a vessel.

In use, the filter sac, struts, and support elements may be compressed and folded to a configuration in which the struts and support elements are proximate the longitudinal axis of the filter whereupon a band 92, omitted from FIGS. 1A-C for clarity (See FIGS. 5 and 6), is advanced over the hub and at least a portion of the struts to hold them in a reduced profile for delivery. The segmented filter mouth provided by the support elements as well as the longitudinal staggering of the support element groups allows the collapsed filter to assume a more compact final diameter than would be the case if a full support hoop were associated with the filter mouth. In addition, this arrangement allows the force necessary to collapse the filter to be lower than would be necessary to collapse a continuous hoop.

Figure 5:
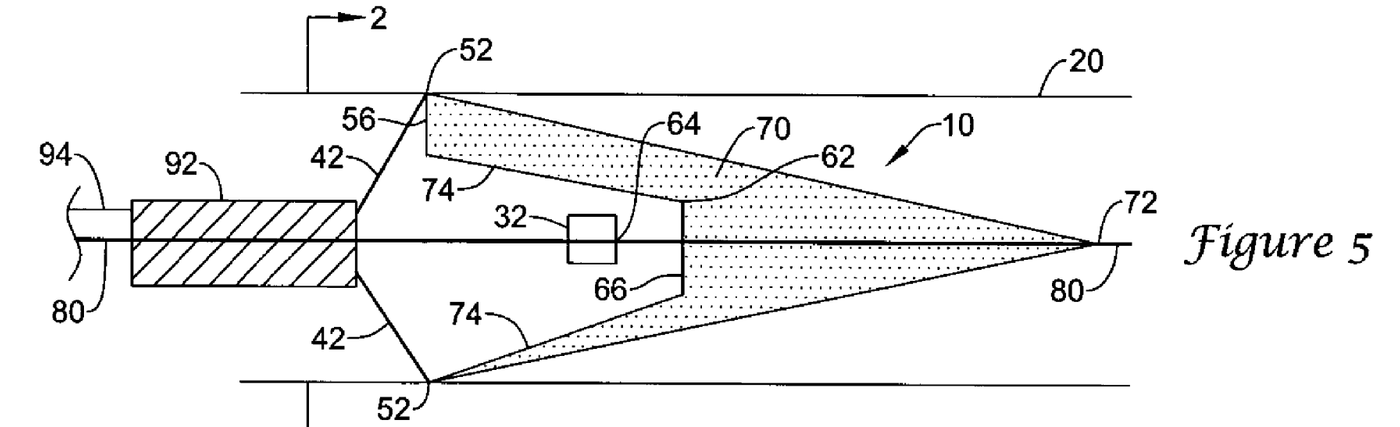
FIG. 5 is a somewhat schematic view of the embodiment of FIG. 1A deployed in a vessel.
Figure 6:
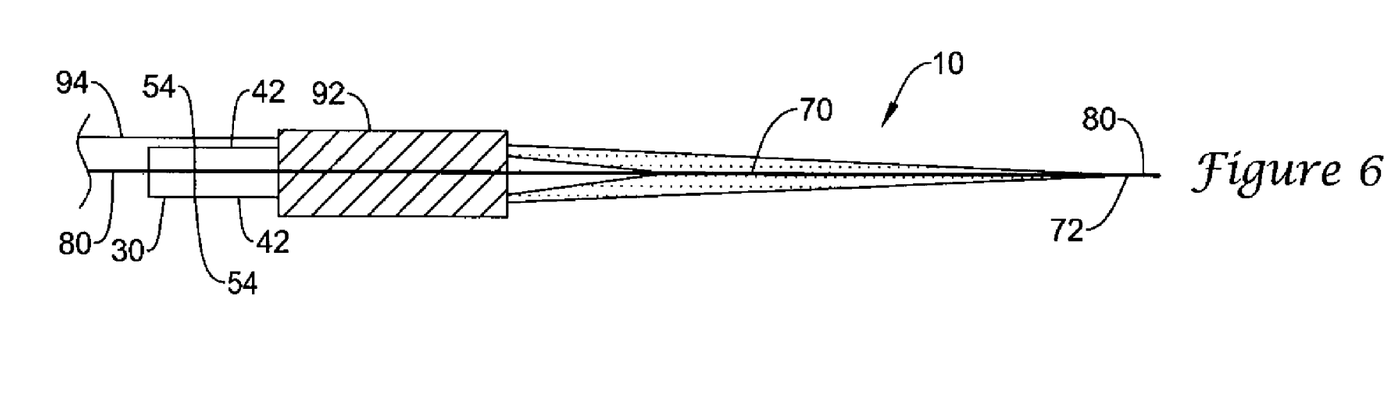
FIG. 6 is a somewhat schematic view of the embodiment of FIG. 5 prior to deployment in a vessel.

Once the filter has been advanced to the portion of the vessel in which it is to be deployed, control element 94 may be translated relative to the filter to remove band 92 from its position restraining the struts (FIG. 6) allowing them to expand to contact the vessel wall thereby deploying the filter sac as illustrated in FIG. 5. The use of a band in combination with a control element such as a wire instead of a delivery sheath may result in an overall reduction in the delivery cross-section of the device allowing it to be used in smaller vessels. It will be appreciated that the filter may be oriented to provide either a distal-facing mouth or a proximal-facing mouth. A proximal-facing filter may be deployed by moving the control element proximally to release the struts and optionally one or both hubs from the band. Similarly, a distal-facing filter may be deployed by moving the control element distally to release the struts and optionally one or both hubs from the band. In some embodiments, the band may encompass both sets of struts in the insertion and removal configuration. In other embodiments, the band may only encompass a single set of struts in the insertion and removal configuration. In yet other embodiments, separate bands may be employed to encompass and release the two sets of struts. In such embodiments, the bands may be moved by either a single control element or by separate control elements. Upon completion of the surgical procedure, the motion of the control element(s) may be reversed to collapse the struts to positions near the longitudinal axis of the filter and the filter together with any entrapped debris may be removed from the vessel.

FIG. 1C illustrates a variation of the filter of FIGS. 1A-B in which the hubs 30 and 32 are mounted on a tubular element 34 having a lumen which coincides with the lumens of the hubs. The tubular element may be confined to a portion of a guidewire 80 passing through the filter by conventional distal and proximal stops (not shown). This arrangement allows the filter to remain undisturbed by small translational or rotational movements of the guidewire which may be incidental to other activity associated with the guidewire such as the advancement of a stent. In some embodiments, the tubular element will extend into the filter sac or even extend beyond the end of the filter sac. In other embodiments, one of the hubs may be configured to slide along the tubular element.

Figure 7:
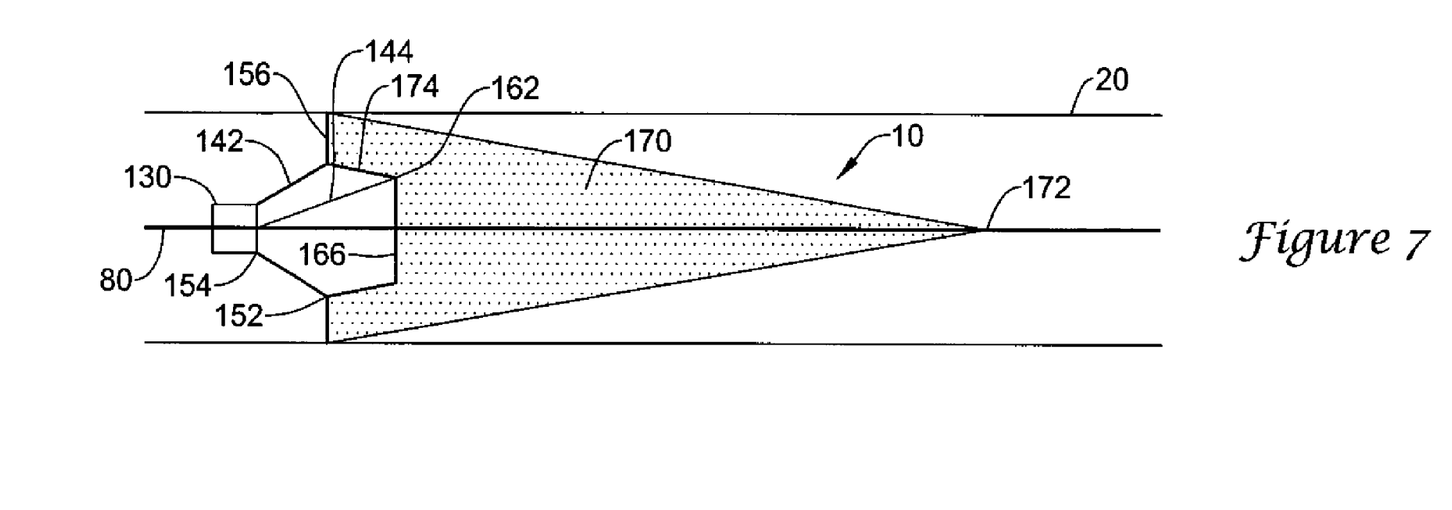
FIG. 7 is a somewhat schematic longitudinal cross-sectional view of an alternate embodiment of the invention deployed in a vessel.
Figure 8:
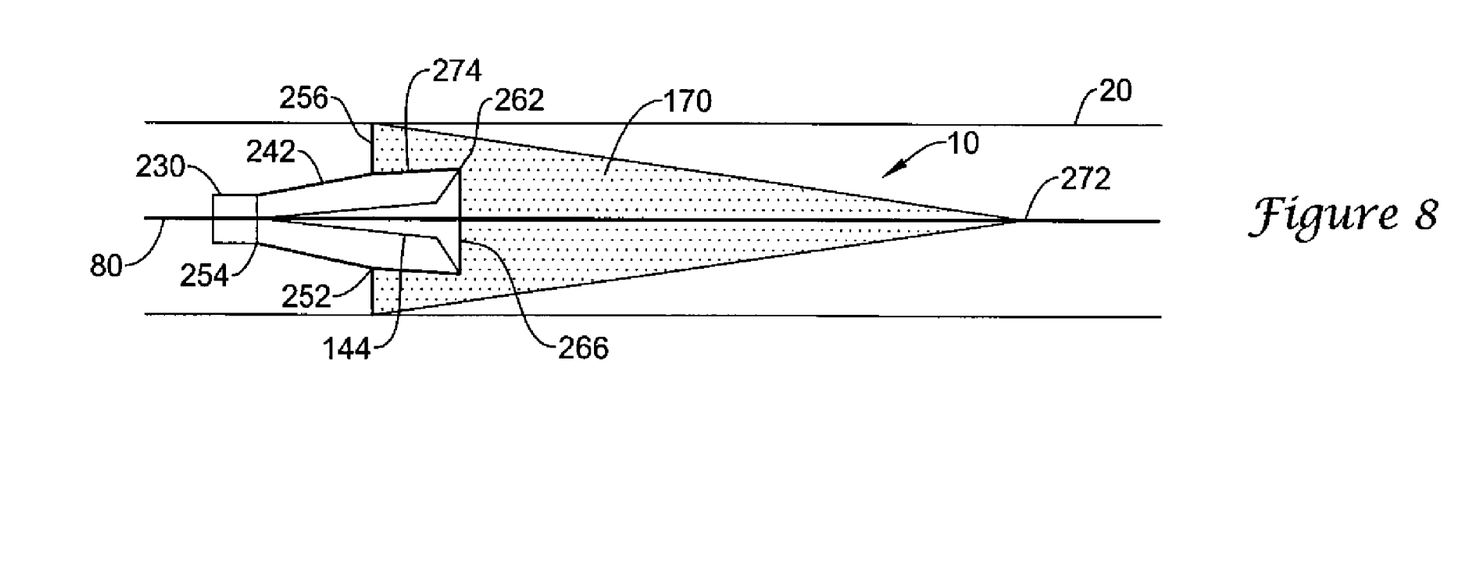
FIG. 8 is a somewhat schematic longitudinal cross-sectional view of an embodiment of the invention deployed in a different vessel.

In addition to embodiments in which axially staggered support element groups are attached to separate pluralities of struts, said struts having equal lengths and attached to separate hubs, embodiments which employ a single hub and two (or more) pluralities of struts having different lengths are also contemplated to reduce complexity while achieving similar results with respect to the placement of the axially spaced-apart support element groups. Such embodiments are illustrated in FIGS. 7 and 8. As illustrated, the strut/support elements of FIG. 7 are "L"-shaped and deployed in a larger vessel while the strut/support elements of related FIG. 8 are paired and bridged by a single support element (FIG. 14) in a smaller vessel. Although not shown in FIGS. 7 and 8, the hub may be attached to a tubular element which extends partially or completely through the filter sac. Such optional tubular elements may be seen in FIGS. 2-4 and FIGS. 9-11.

In FIG. 7, each "L"-shaped strut/support element assembly is attached to a single hub 130. A first set of two struts 142, each bearing support elements 156, support and deploy the proximal portion of the filter mouth while a second, longer set of two struts 144, also connected to hub 130, support and deploy the distal portion of the filter mouth. Edge segments 174 of the filter membrane remain unsupported and complete the mouth of the filter sac 170.

In FIG. 8, each support element 256 or 266 is attached to hub 230 by a pair of struts. Two proximal support elements 256 are attached to hub 230 by struts 142 having first ends 254 and distal ends 252. Two distal support elements 266 are attached to hub 230 by struts 144 having first ends 264 and distal ends 262. Filter sac 270 is attached alternately to the support elements leaving generally axial segments 274 unattached therebetween. Note that the lengths of the unattached edges 174 and 274 of the filter sacs are nearly the same in the larger diameter vessel of FIG. 7, in which gaps would appear between support segments as viewed in the longitudinal direction, and in the smaller diameter vessel of FIG. 8 in which overlaps would appear in a similar view. As in FIG. 7, the mouth of the filter sac of FIG. 8 alternately comprises segments supported by support elements and unsupported edges and segments of the proximal group of support segments alternate with segments of the distal group of support segments. It will be appreciated that embodiments which include three sets of struts or even four sets of struts, each set differing in nominal length from the lengths of the first and second set of struts of FIGS. 7 and 8, to define third or fourth planes of support elements may be employed by analogy to the embodiments described above which employ more than two hubs.

Figure 3:
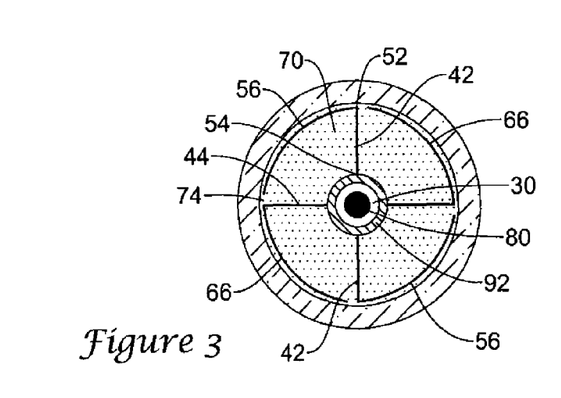
FIG. 3 is a somewhat schematic axial view in the distal direction of an embodiment of the invention deployed in a vessel.
Figure 9:
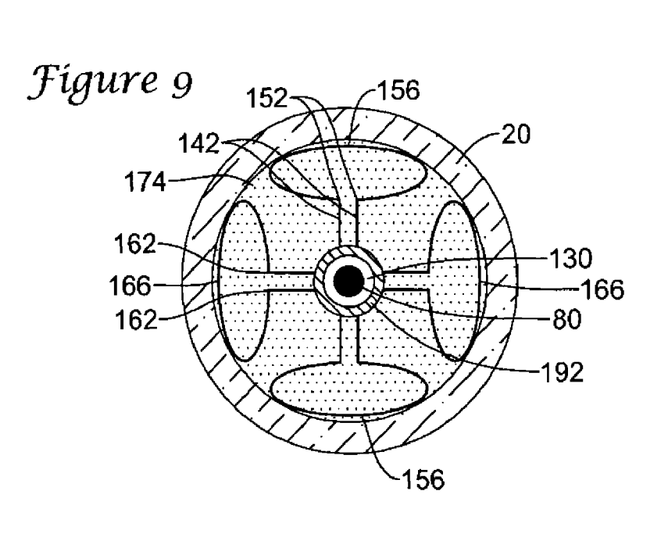
FIG. 9 is a somewhat schematic axial view in the distal direction of an embodiment of the invention deployed in a vessel.
Figure 10:
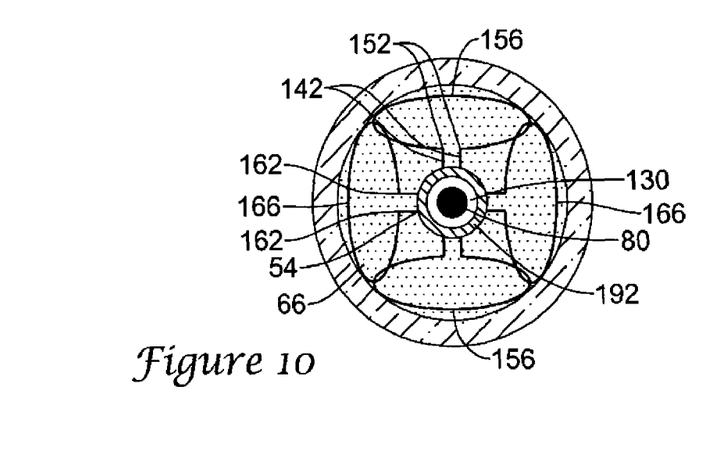
FIG. 10 is a somewhat schematic axial view in the distal direction of an embodiment of the invention deployed in a vessel.
Figure 11:
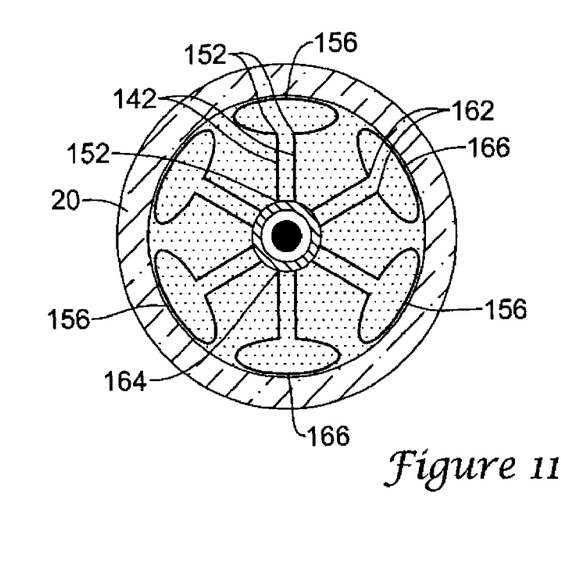
FIG. 11 is a somewhat schematic axial view in the distal direction of an embodiment of the invention deployed in a vessel.

FIGS. 9-11 are similar to FIGS. 2-4 except that each support segment is associated with two struts (FIG. 14) rather than just one. Paired struts may provide additional stability to the support segment and may retract both ends of the support segment simultaneously while tending to wrap the support segment around the guidewire. Although the embodiments of the figures have included support segments of equal length separated by equal gaps, it will be appreciated that the arc lengths of the support segments may differ within a group and/or between groups and that the gaps/overlaps which are spanned by unsupported edges need not all have the same circumferential extent. Unequal arc lengths or gaps may be desirable, for example, if the guidewire is not centered within the vessel. Although the groups of support segments generally are disposed in parallel planes normal to the axis of the filter, the planes may be moderately tilted with respect to each other and/or with respect to the longitudinal axis of the filter without departing from the spirit of the invention. FIG. 11 illustrates an embodiment in which three proximal support elements 166 and three distal support elements 156 are attached to a single proximal hub.

In some embodiments, the filter is held in a delivery configuration by a band which surrounds at least a portion of the struts holding them near the longitudinal axis of the filter. The band may also encompass at least some of the support elements and a portion of the filter sac. In other embodiments, two or more bands may be employed. The band or bands may be withdrawn and advanced by a control element such as a wire. When more than one band is employed, the bands may share a control element or may each have their own control element. Separate control elements associated with multiple bands may provide additional control over the deployment of the filter and/or may be used to ensure that debris remains trapped within the sac by closing the mouth portions sequentially. The use of a control element in conjunction with a band may result in a smaller delivery cross-section than would be possible with a filter which is deployed in a conventional sheath or catheter; however a sheath may be used with the filters of the invention if desired and may even replace the band and control element.

In some embodiments, the filter may be advanced over a previously positioned guidewire. In other embodiments, each of the hubs of the filter may be fixed in place in a spaced-apart relationship relative to a guidewire, or tubular element, by soldering, welding, adhesives, or the like. When multiple hubs are present and are spaced-apart by slightly more than the length of the first struts and associated support elements, the filter may be capable of contracting to a smaller cross-sectional area than would be the case if the first struts overlap the second hub. In yet other embodiments, one or more hubs may remain free to translate relative to the guidewire or tubular element. Certain embodiments with a fixed hub and one or more hubs capable of limited motion relative to a guidewire or tubular element may be able to accommodate to a wider range of vessel diameters without requiring an elastic filter sac.

Various modifications and alterations of this invention will become apparent to those skilled in the art without departing from the scope and principles of this invention, and it should be understood that this invention is not to be unduly limited to the illustrative embodiments set forth hereinabove. Although the illustrative examples described above relate to an embodiment in which the open mouth of the filter is directed proximally with respect to the guide wire, a reversal of the filter components is also contemplated. All publications and patents are herein incorporated by reference to the same extent as if each individual publication or patent was specifically and individually indicated to be incorporated by reference.

What is claimed is:

1. An embolic filter comprising:
    a first hub having an axial lumen therethrough, said lumen defining a longitudinal axis of the filter and adapted to receive a guidewire therethrough;
    a second hub having an axial lumen therethrough, said lumen coinciding with the longitudinal axis of the filter and adapted to receive a guidewire therethrough wherein the first and second hubs are displaced along the longitudinal axis;
    a first plurality of struts each having a first end, a second end, and a length, said first ends being directly connected to the first hub and the said second ends of the first plurality of struts being biased to expand away from the longitudinal axis of the filter;
    a second plurality of struts each having a first end, a second end, and a length, said first ends directly connected to the second hub and the said second ends of the struts being biased to expand away from the longitudinal axis of the filter, wherein the lengths of the first plurality of struts is substantially the same as the lengths of the second plurality of struts and the two pluralities of struts assume equivalent angles with the longitudinal axis in an expanded state;
    at least a first population and a second population of support elements directly connected to the second ends of the respective first and second pluralities of struts such that each population of support elements defines a plane transverse to the longitudinal axis of the filter, said planes being relatively displaced along the longitudinal axis of the filter;
    a filter sac attached at an open end to the first population and the second population of support elements and having a closed end extending beyond the planes defined by the first population and the second population of support elements;
    wherein the filter sack includes a plurality of edges not attached to the populations of support elements, said plurality of edges not attached to the populations of support elements and the first and second populations of support elements defining the open end of the filter sac,
    further wherein each circumferentially alternate edge not attached to the populations of support elements connects a support element of the first population of support elements to a support element of the second population of support elements such that following the open mouth of the filter sac alternates in the distal to proximal and then proximal to distal direction along the edges not attached to the populations of support elements;
    at least one band element slidable over the hubs and the struts thereby moving those portions of the struts which are coupled to the support elements closer to the longitudinal axis of the filter; and
    a control element attached to the band, said control element adapted to move the band along the longitudinal axis of the filter and over at least a portion of the longitudinal struts.

2. The embolic filter of claim 1, further comprising a second band and attached control element.

3. The embolic filter of claim 1, further comprising a guidewire disposed within the lumen of the first hub and the lumen of the second hub.

4. The embolic filter of claim 3, wherein the first hub is fixedly attached to the guidewire.

5. The embolic filter of claim 4, wherein the second hub is fixedly attached to the guidewire.

6. The embolic filter of claim 1, further comprising a tubular element having a longitudinal lumen therethrough, said lumen sized to receive a guidewire.

7. The embolic filter of claim 6, wherein the first hub and the second hub are fixed to the tubular element in a spaced apart relationship.

8. The embolic filter of claim 6, further comprising a guidewire passing through the axial lumen of the tubular element.

9. The embolic filter of claim 8, wherein the tubular element is free to rotate and translate with respect to at least a portion of the guidewire.

10. The embolic filter of claim 9, wherein the portion of the guidewire with respect to which the tubular element is free to rotate and translate is defined by proximal and distal stops coupled to the guidewire.

* * * * *